United States Patent [19]

Hirsh

[11] Patent Number: 5,113,911
[45] Date of Patent: May 19, 1992

[54] PRESSURE ACTUATED ELASTOMERIC VALVE

[75] Inventor: Robert Hirsh, Philadelphia, Pa.

[73] Assignee: Advantec Corp., Philadelphia, Pa.

[21] Appl. No.: 713,036

[22] Filed: Jun. 7, 1991

Related U.S. Application Data

[63] Continuation of Ser. No. 449,275, Dec. 11, 1989, abandoned.

[51] Int. Cl.⁵ ............................................. F16K 15/14
[52] U.S. Cl. .................................. 137/844; 251/212
[58] Field of Search ............... 251/212, 120; 137/843, 137/844, 845, 852; 138/45

[56] References Cited

U.S. PATENT DOCUMENTS

| | | |
|---|---|---|
| 2,135,237 | 11/1938 | Lewis et al. ..................... 251/212 |
| 2,752,951 | 7/1956 | Silverstein ........................ 138/45 |
| 2,922,437 | 1/1960 | Rippingille ...................... 137/844 |
| 3,301,443 | 1/1967 | Clancy et al. ................ 137/852 X |
| 3,336,000 | 8/1967 | Barber ............................. 251/212 |
| 4,143,853 | 3/1979 | Abramson . |
| 4,334,551 | 6/1982 | Pfister ........................ 137/614.03 |
| 4,341,239 | 7/1982 | Atkinson . |
| 4,346,704 | 8/1982 | Kulle . |
| 4,434,810 | 3/1984 | Atkinson . |
| 4,439,182 | 3/1984 | Huang . |
| 4,475,898 | 10/1984 | Brodner et al. . |
| 4,549,879 | 10/1985 | Groshong et al. . |
| 4,657,536 | 4/1987 | Dorman . |
| 4,752,287 | 6/1988 | Kurtz et al. . |
| 4,753,640 | 6/1988 | Nichols et al. . |
| 4,765,588 | 7/1988 | Atkinson . |

FOREIGN PATENT DOCUMENTS

| | | | |
|---|---|---|---|
| 269907 | 2/1914 | Fed. Rep. of Germany .......... | 251/4 |
| 30452 | 7/1926 | France ..................................... | 251/8 |

Primary Examiner—John C. Fox
Attorney, Agent, or Firm—Caesar, Rivise, Bernstein, Cohen, & Pokotilow, Ltd.

[57] ABSTRACT

A valve is provided for controlling fluid flow through a flow path, such as a conduit, duct or tubing. The valve includes at least two gate members which abut each other at a fluid-tight interface, so that fluid flow past or through the gate members is prohibited. The gate members are made of resilient elastomeric material which is compressible under fluid pressure in order to force the gate members apart at their interface and, thus, allow fluid to pass therebetween. The invention also includes a flow connector and valve combination for controlling the introduction of additional fluid into the single flow path created within the connector.

10 Claims, 3 Drawing Sheets

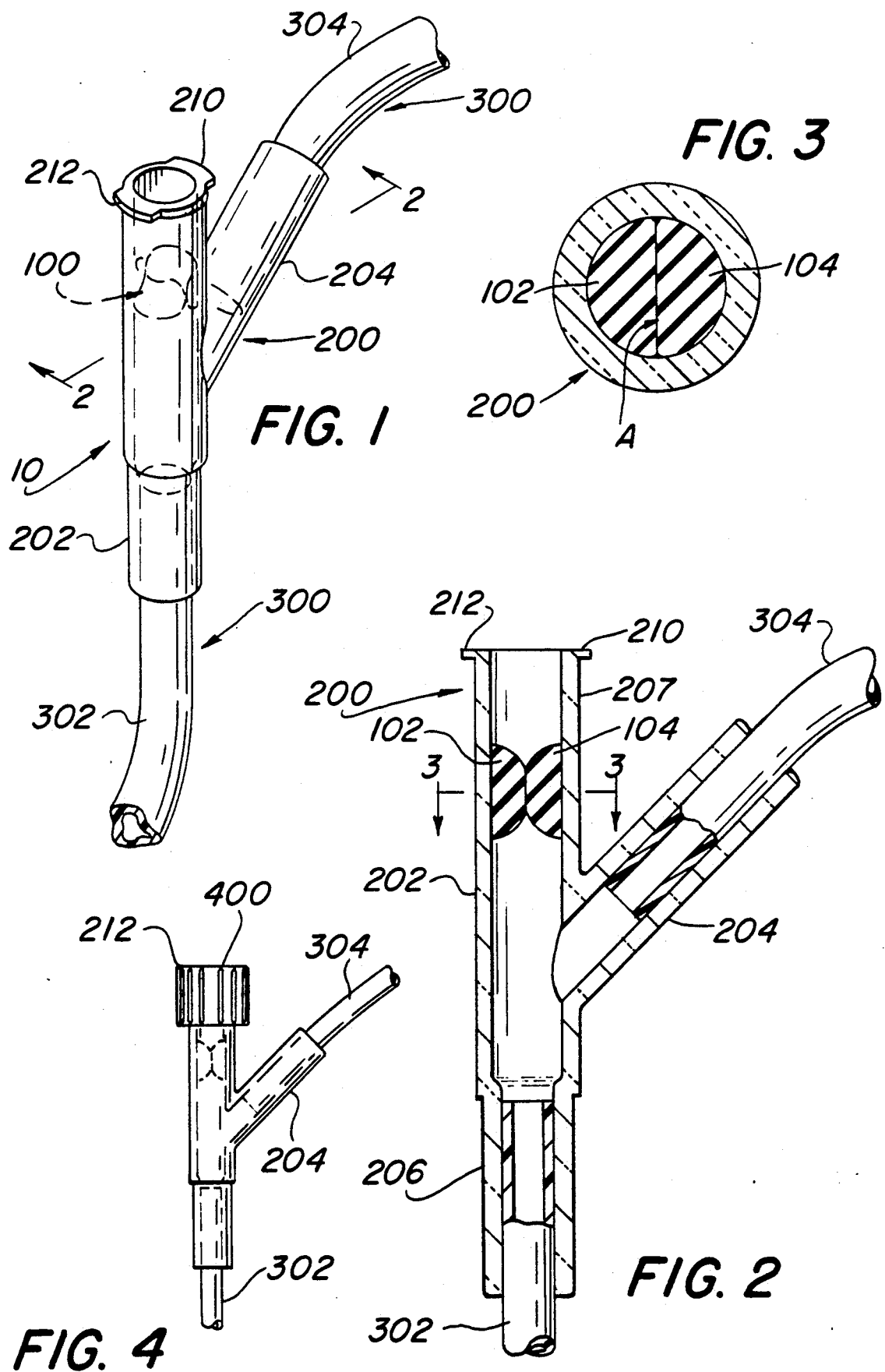

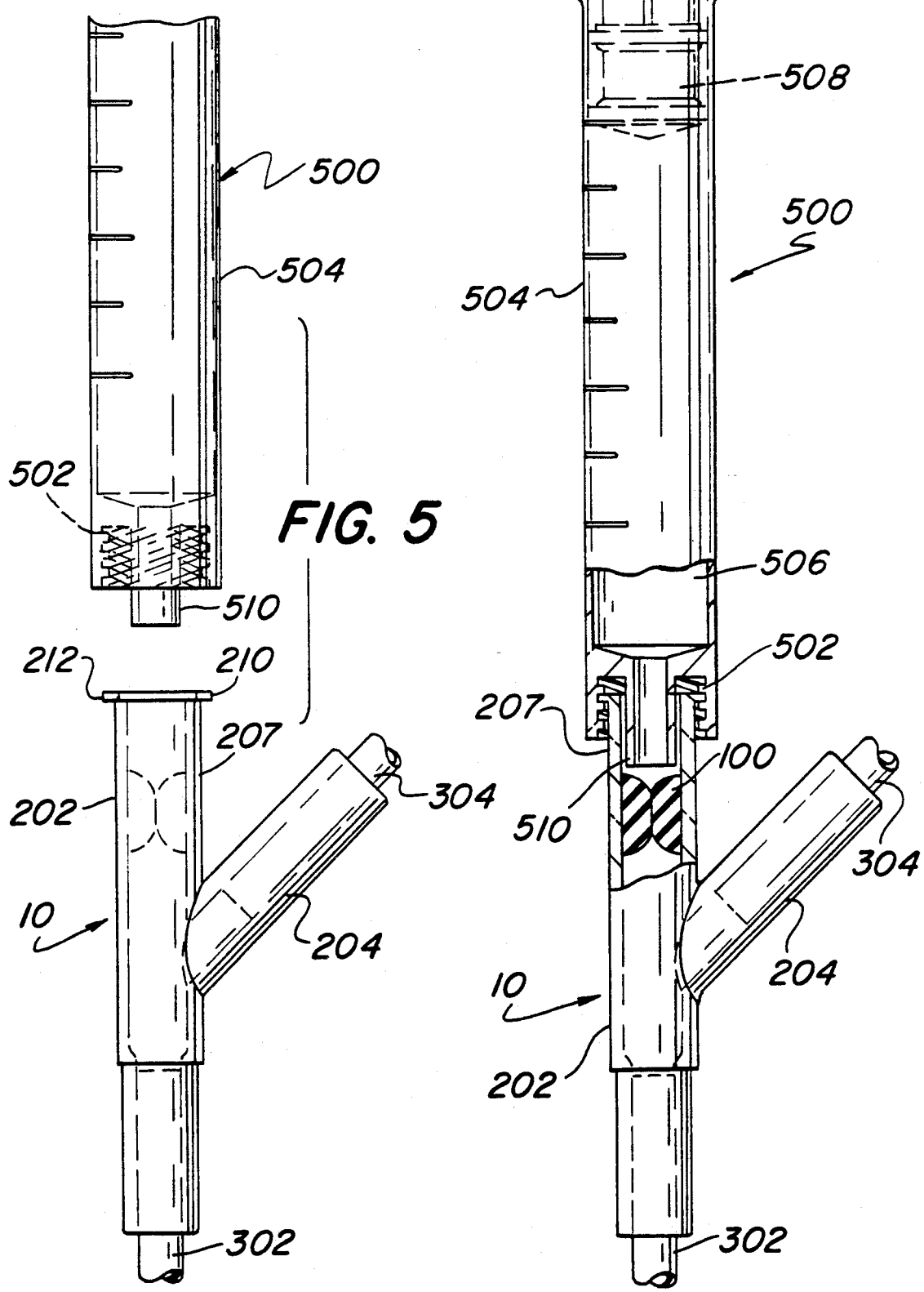

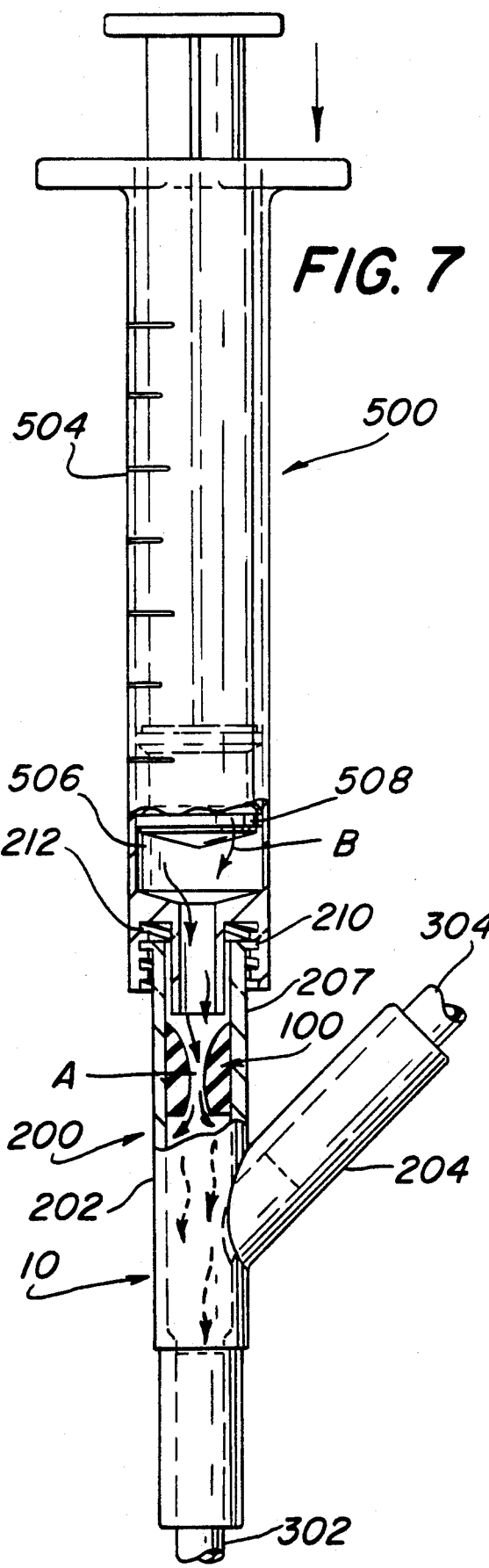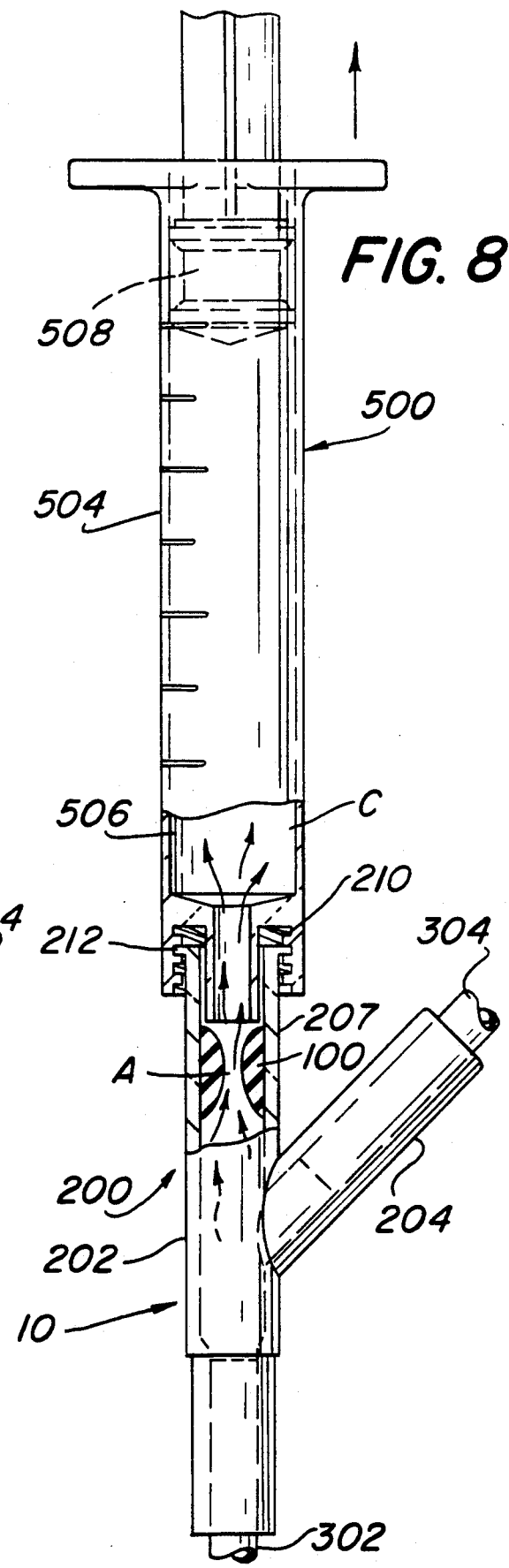

PRESSURE ACTUATED ELASTOMERIC VALVE

This application is a continuation of application Ser. No. 07/449,275, filed Dec. 11, 1989, now abandoned.

FIELD OF THE INVENTION

The present invention relates to flow valves for use in fluid pathways, such as conduits, and in particular, the invention relates to a pressure-actuated elastomeric valve for use in controlling liquid flow in intravenous tubing.

BACKGROUND OF THE INVENTION

The necessity of providing drugs and other solutions to patients in a continuous intravenous fashion is well recognized. In the simplest arrangement, the intravenous injection of drugs or other materials is achieved by establishing the intravenous introduction site into the patient, providing a source of the material or substance, e.g. a drug, to be intravenously introduced into the patient and providing a conduit or tubing between the source and the introduction site through which the material is transmitted to the introduction site.

Oftentimes, it is necessary or at least desirable to introduce a second material into the conduit so that it will flow along with the primary flow of the first material into the patient through the intravenous connection. One method of introducing the second material into the conduit is to provide a multi-branched connector in the conduit in order to allow the second material to be introduced into the conduit through one of the branches of the connection, while the primary flow also passes therethrough.

Any branches of the multi-branched connector used to introduce the second material must be kept closed to maintain sterile conditions and to prohibit the introduction of unnecessary and sometimes harmful fluids through the connector. For this reason, the open branches of the connector usually contain some form of seal. In order to introduce the second material into the conduit the seal in the second branch must be overcome.

One example of a type of seal which may be used is an elastomeric bung positioned over or within the second branch of the connector. In order to introduce the second material into the intravenous feed conduit using this multi-branched connector, a hypodermic needle is inserted through the bung and by means of a syringe connected to the needle, the second material contained in the syringe is injected into the connector and into the intravenous feed conduit.

Another example of a type of seal which is used to prevent introduction of undesired materials into the intravenous conduit when a multi-branch connector is used is to insert into the branch(es) of the connector a one-way valve which requires a specific pressure thereagainst in order to permit any secondary material, whether desired or not, to enter the branch of the connector and ultimately the conduit to the intravenous connection.

These two types of seals have significant drawbacks which need to be overcome. One of the most important drawbacks of using the bung seal in the connector is the necessity of injecting the additional material with a sharp needle. At this time, when the risk of communicable diseases such as hepatitis, AIDS and other viral diseases is great, any use of needles which might result in the puncture of the person administering the material is to be avoided if at all possible. Because the bung is usually very small, the chance of pricking a finger with a needle is substantial. Accordingly, any system for injecting additional material into the intravenous conduit without the necessity of using a needle will be beneficial.

Another drawback is the fact that the presently available systems which incorporate one-way valves require costly materials and construction, since many of these valves are spring-biased. In this regard, it is important that any seal be economical as well as needleless.

There are known several different types of seals or valves which are either one-way or bi-directional and which operate on hydrostatic pressure. Examples of these valves which are patented include: the valve disclosed in Nichols et al., U.S. Pat. No. 4,753,640, which includes a catheter tube of elastomeric material having lumen shapes and slit valves; and the valve taught in Kulle, U.S. Pat. No. 4,346,704, which is a one-way sleeve valve for parenteral solution injection and comprises an outer housing defining an outlet tube and an inner tubular support defining an inlet tube. Furthermore, in the Huang patent, U.S. Pat. No. 4,439,182, a valvular infusion device having valve chambers and resilient one-way valve means which minimize volumetric dead space in disclosed. The device permits one-handed, needleless injection of drugs utilizing commonly known IV apparatus. The patent to Dorman, U.S. Pat. No. 4,657,536, discloses a check valve catheter comprising a central bore and a cross bore or port covered by a thick elastic sleeve to create a check valve. In the Brodner et al. patent, U.S. Pat. No. 4,475,898, a fetal ventriculo-amniotic shunt comprised of a tubular body having a slit-type valve for fluid flow-through is disclosed, and in the Groshong et al. patent, U.S. Pat. No. 4,549,879, a catheter comprising a flexible material with a closed end is taught. A single slit in the Groshong patent catheter wall acts as a pressure actuated valve to permit fluid flow therethrough. Other patents which generally disclose such valves include the Kurtz et al. patent, U.S. Pat. No. 4,752,287, the Atkinson patents, U.S. Pat. Nos. 4,434,810, 4,765,588 and 4,341,239, and the patent to Abramson, U.S. Pat. No. 4,143,853.

OBJECTS OF THE INVENTION

With the above background in mind, it is a primary object of the invention to provide a pressure-activated elastomeric valve which is adaptable for use in a connector for intravenous use.

It is also an object of this invention to provide a pressure-actuated elastomeric valve which is capable of one-way or two-way operation.

It is a further object of this invention to provide an elastomeric valve which eliminates the need for the use of needles to inject material through the seal of the valve, but which is also able to have a needle inserted therethrough in an emergency where there is an immediate need to pierce through the valve seal to inject material into the intravenous conduit.

It is another object of this invention to provide a connector and pressure actuated elastomeric valve which can be easily connected to a syringe for needleless injection or removal of fluid through the elastomeric valve in the connector.

It is a further object of the invention to provide a pressure-actuated elastomeric valve and connector plus valve which are economical to manufacture.

SUMMARY OF THE INVENTION

In furtherance of these objectives, a valve is provided for controlling fluid flow through a flow path, such as a conduit, duct or tubing. The valve includes at least two gate members which abut each other at a fluid-tight interface, so that fluid flow past or through the gate members is prohibited. The gate members are made of resilient elastomeric material which is compressible under fluid pressure in order to force the gate members apart at their interface and, thus, allow fluid to pass therebetween.

The invention also includes a flow connector wherein the valve is positioned. The connector interconnects at least two fluid flow paths into a single flow path and the valve member is positioned in the connector to control the introduction of additional fluid from at least one other flow path into the single flow path.

BRIEF DESCRIPTION OF THE DRAWINGS

Other objects and many of the attendant advantages of the instant invention will be readily appreciated as the same become understood by reference to the following detailed description when considered in conjunction with the accompanying drawings, wherein:

FIG. 1 is an isometric view of the connector of the present invention showing the valve of the present invention thereinside;

FIG. 2 is an enlarged sectional view taken along the line 2—2 in FIG. 1;

FIG. 3 is an enlarged sectional view taken along the line 3—3 in FIG. 2;

FIG. 4 is a side view of the connector and valve of the present invention with a cover positioned thereon;

FIG. 5 is a side view of the connector and valve of the present invention and a syringe for attachment thereto;

FIG. 6 is a partially cut-away side view of the syringe and connector showing a syringe positioned on the connector of the present invention;

FIG. 7 is a partially cut-away side view of the syringe and connector showing the flow of fluid out of the syringe through the open valve member; and FIG. 8 is a partially cut away side view of the syringe and connector showing the withdrawal of fluid into the syringe through the open valve member.

DETAILED DESCRIPTION OF THE PREFERRED EMBODIMENT

Referring now to the formal drawings where like features are denoted by like reference characters, the connector and elastomeric valve combination of the present invention is generally shown at 10 in FIG. 1. In the preferred embodiment, a valve, designated generally as 100, is provided for use within a connector, designated generally as 200, which is connected to intravenous tubing 300. As will be discussed herein, the environment for usage of the valve need not be limited to a connector for use with intravenous tubing or intravenous fluid flow.

As shown in FIGS. 1, 2 and 4, the connector 200 is hollow, tubular and generally Y-shaped with a vertical section 202 and an intersecting angled section 204. Fitted into the lower end 206 of the vertical section 202 is a first tube 302, and fitted into the angled section 204 is a second tube 304. Both the first and second tubes are securely held within the connector sections 202, 204 in any manner which is well known within the art; however, molding the tubing directly to the connector is preferred. At the top end 208 of the vertical section is a luer flange 210. The luer flange is used to attach a cover 212 (FIG. 4) onto the connector, or as shown in FIGS. 5-8, a syringe 500 may be attached by means of the luer flange to the connector 200.

The lower end 206 of the vertical section 202 provides a first fluid flow path and the angled section 204 provides a second fluid flow path. The connector 200 brings these two flow paths together to form one path. The upper end 207 of the vertical section 202 provides a third fluid path which enters into the single path created by the lower end 206 and the angled section 204.

Stationarily positioned within the upper end 207 of the vertical section 202 of the connector and spaced below the top end 208 thereof is the valve 100. As shown in FIGS. 2 and 3, the valve 100 is comprised of at least a two confronting D-shaped gate members 102, 104. The two D-shaped gate members 102, 104 are made of elastomeric material. The two D-shaped members 102, 104 confront each other as shown at A in FIGS. 2 and 3 and form a fluid-tight engagement under static or standard conditions which completely prohibits fluid flow through the vertical section 202 of the connector 200. Even though the valve 100 is fluid-tight, the cap 212 is provided to insure that contaminants do not come into contact with the valve members prior to use. The cap 212 is designed internally (not shown) in a manner which is known to enable the cap to mate with the luer flange 210 when the cap is urged downward and rotated about the flanges in order to retain the cap on the connector. Reverse rotation of the cap on the leur flanges causes the cap to be removed from the connector 200, thus exposing the valve 100.

An example of the use of the connector 200 and valve 100 combination is shown in FIGS. 5-8. A syringe 500 is provided for engagement with the connector 200. The syringe 500 is of standard construction, that is, it has an internal end configuration 502 which allows it to be fitted securely onto the leur flange 210 on the connector 200. The syringe body 504 is hollow with a chamber 506 therein, and a plunger 508 tightly and slidably fits within the chamber 506. FIG. 6 shows the syringe 500 secured onto the connector 200 at the luer flange 210 of the connector.

Prior to positioning the syringe 500 onto the connector 200, the chamber 506 of the syringe is filled with the fluid, e.g., a liquid drug, which is to be transferred into the connector 200. One method of filling the syringe 500 which is known is to withdraw the plunger 508 in the chamber 506 in order to draw into the chamber the fluid which will be transferred into the connector 200 through the opening 510 at the end of the syringe. Other methods of providing a filled syringe are also well known.

As shown in FIG. 7, the plunger 508 is forced through in the chamber 506 and the fluid within the chamber, designated generally by the arrows B, is forced out of the chamber against the valve 100. The hydrostatic pressure of the fluid B urging against the D-shaped gates 102, 104 causes the gates to separate at their interface A and allows the fluid B to pass therethrough toward the single flow path created by the lower end 206 and the angled section 204. The amount of force required to separate the gates 102, 104 will, of course, depend on the density, bulk modulus of elasticity and other physical properties of the specific elastomer selected to form the valve gates. When the force is diminished, the gates will expand under their own resiliency to again form a fluid-tight interface at A.

The valve 100 and connector 200 combination can be used to allow withdrawal of fluid from the single flow path as well as be used for injection of fluid thereinto. FIG. 8 shows the plunger 508 being pulled outward through the chamber 506, thus creating a vacuum within the chamber 506 and causing the fluid in the lower end 206, generally shown as arrows C, to urge against the D-shaped gates 102, 104 and force them apart at their interface A. The fluid C flows into the chamber 506 until the natural resiliency of the gates is no longer overcome by the flow of the fluid C created by the vacuum, at which point the gates return to their fluid-tight interface position A.

While a significant feature of the invention is the ability to inject fluid into intravenous tubing without using a connector containing a bung through which a sharp needle must be inserted, it is recognized that there are oftentimes emergency situations when there is not sufficient time to fill a needleless syringe, fasten it to the luer flange of the connector and the force the fluid out of the syringe through the gates. In those situations, with the present invention, because of the elastomeric composition of the gates, it is possible to rapidly insert a needle directly through the gates to inject the fluid therethrough. This is not possible with many types of prior one-way or two-way valve constructions which utilize mechanical valve constructions through which it is impossible to insert a needle.

It is also possible to utilize the specific valve construction of opposing D-shaped gates of elastomeric material in environments other than within a connector for use with intravenous tubing. For example, in addition to intravenous tubing the valve may be used in any other conduit such as a pipe or duct, and may serve as a safety release valve. When fluid pressure on one side or the other of the valve becomes sufficient to force the D-gates apart from their fluid-tight engagement, the gates will open and allow the fluid under pressure to dissipate therethrough until the pressure is no longer great enough to force the gates apart.

Without further elaboration, the foregoing will so fully illustrate my invention that others may, by applying current or future knowledge, adopt the same for use under various conditions of service.

I claim as my invention:

1. A two-way fluid control device for use in a fluid flow path, some fluid control device comprising:
   a first gate within said fluid flow path;
   at least one second gate within said fluid flow path, said second gate abutting said first gate and forming a fluid-tight interface at said abutting location which completely obstructs said flow path; and
   said first and second gates being comprised of a solid mass of resilient elastomeric material which is compressible under fluid pressure and said gates being positioned totally within said fluid flow path.

2. A two-way fluid control device as claimed in claim 1, wherein said first and second gates have a D-shaped longitudinal cross-section, and said first and second gates abut each other at the curved portion of their longitudinal D-shaped cross-sections.

3. A two-way fluid control device as claimed in claim 1, wherein:
   said fluid flow path is a conduit; and
   said first and second gates are positioned within said conduit.

4. A two-fluid actuated valve comprising:
   a first gate comprised of a solid mass of elastomeric material;
   a second gate comprised of a solid mass of elastomeric material abutting said first gate and forming a fluid-tight seal at said abutting location; and
   said first and second gates being compressible from their abutting position under fluid pressure.

5. A two-way fluid actuated valve as claimed in claim 4, wherein said first and second gates have a D-shaped longitudinal cross-section, and said first and second gates abut each other at the curved portion of their longitudinal D-shaped cross-sections.

6. A device for connecting at least two fluid flow paths into a single flow path and for controlling the fluid flow of at least one third fluid flow path into and out of said single fluid flow path, said device comprising:
   connecting means for connecting a first fluid flow path to a second fluid flow path and bringing said first and second fluid flow paths into communication with each other to form a single flow path, said connecting means having at least three openings thereinto, the first and second of said openings being connected, respectively, to said first and second flow paths;
   two-way valve means within and spaced from a third opening in said connecting means for controlling fluid flow of a third flow path into and out of said first and second flow paths in communication with each other, said valve means being comprised of:
   a first gate within said third fluid flow path;
   at least one second gate within said third fluid flow path, said second gate abutting said first gate and forming a fluid-tight interface at said abutting location which completely obstructs said third flow path; and
   said first and second gates being comprised of a solid mass of resilient elastomeric material which is compressible under fluid pressure and said gates being positioned totally within said third fluid flow path.

7. A device as claimed in claim 6, wherein said first and second gates have a D-shaped longitudinal cross-section, and said first and second gates abut each other at the curved portion of their longitudinal D-shaped cross-sections.

8. A device as claimed in claim 6, wherein:
   said connecting means is comprised of a Y-shaped member having first, second and third openings thereinto at respective ends of said Y-shape, said first and second openings being connected, respectively, to said first and second fluid flow paths;
   said first and second fluid flow paths are comprised of tubular conduits fitted at one end into said first and second openings; and
   valve means is fitted into said Y-shaped member a distance spaced from said third opening.

9. A device as claimed in claim 8, further comprising cover means over said third opening for covering said third opening.

10. A device as claimed in claim 9, wherein:
    said third opening has a luer flange therearound; and
    said covering means comprises a cap having internal threadings adapted to fit said luer flange around said third opening.

* * * * *